United States Patent

Wahl et al.

[11] Patent Number: 6,008,895
[45] Date of Patent: Dec. 28, 1999

[54] STOICHIOMETRIC RATIO MEASURING DEVICE

[75] Inventors: Claus Wahl, Vaihingen; Juergen Steinwandel, Uhldingen-Muehlhofen, both of Germany

[73] Assignee: Deutsches Zentrum Fuer Luft -und Raumfahrt e.V., Bonn, Germany

[21] Appl. No.: 09/055,869

[22] Filed: Apr. 6, 1998

Related U.S. Application Data

[63] Continuation of application No. PCT/EP97/04244, Aug. 5, 1997.

[30] Foreign Application Priority Data

Aug. 13, 1996 [DE] Germany .......................... 196 32 607

[51] Int. Cl.$^6$ .............................. G01J 3/30; G01J 31/14; G01N 21/00; G01N 7/00
[52] U.S. Cl. ......................... 356/311; 356/315; 356/341; 356/417; 356/307; 73/23.31; 250/343; 250/341.6; 250/339.08; 250/554
[58] Field of Search ..................................... 356/313, 316, 356/317, 318, 417, 71, 72, 311, 312, 314; 250/271, 343, 458.1, 459.1, 461.1, 461.2, 339.13, 339.14, 341.6, 339.08

[56] References Cited

U.S. PATENT DOCUMENTS

| | | |
|---|---|---|
| 3,887,280 | 6/1975 | McLean . |
| 4,078,178 | 3/1978 | Lowes ...................................... 250/336 |
| 4,300,834 | 11/1981 | Demers et al. .......................... 356/315 |
| 4,392,236 | 7/1983 | Sandstrom et al. ..................... 250/271 |
| 4,415,264 | 11/1983 | Wittmer .................................. 356/315 |
| 4,444,169 | 4/1984 | Kirisawa et al. . |
| 4,479,499 | 10/1984 | Alfano .................................... 356/317 |
| 4,549,080 | 10/1985 | Baskins et al. .......................... 250/343 |
| 4,692,875 | 9/1987 | Riley et al. . |
| 4,718,028 | 1/1988 | Gussin et al. ............................ 364/572 |
| 4,896,965 | 1/1990 | Goff et al. . |
| 4,959,549 | 9/1990 | Haub et al. . |
| 5,333,487 | 8/1994 | Kimura et al. .......................... 356/313 |
| 5,473,162 | 12/1995 | Busch et al. ............................ 356/311 |
| 5,840,582 | 11/1998 | Ngan ....................................... 356/317 |

FOREIGN PATENT DOCUMENTS

| | | |
|---|---|---|
| 43 05 645 | 8/1994 | Germany . |
| 44 02 310 | 8/1995 | Germany . |

OTHER PUBLICATIONS

Sappey, Andrew D. et al., "Laser–Induced Fluorescence Detection of Singlet $CH_2$ in Low–Pressure Methane/Oxygen Flames," *Applied Physics B*, Springer–Verlag, 1990, pp. 463–472.

Patent Abstracts of Japan, Abstract of Japanese Patent No. 2–212746, "Combustion Light Type Air/Fuel Ratio Sensor", P–1128, vol. 14, No. 508, Nov. 7, 1990.

*Primary Examiner*—F. L. Evans
*Assistant Examiner*—Roy M. Punnoose
*Attorney, Agent, or Firm*—Barry R. Lipsitz; Ralph F. Hoppin

[57] ABSTRACT

In order to provide a measuring device for determining stoichiometric ratios when burning hydrocarbons by means of which stoichiometric ratios can be determined easily and reliably when burning hydrocarbons, it is proposed that a sensor be provided to detect an intensity of a first fluorescent radiation from C—H molecular fragments arising during the burning and a sensor be provided to detect an intensity of a second fluorescent radiation from molecular fragments arising during the burning and comprising only C atoms, that the sensors generate an intensity-dependent first and second sensor signal, respectively, on the basis of the first and the second fluorescent radiation, and that an evaluation circuit be provided which generates an output signal corresponding to a stoichiometric ratio from a ratio between the intensities of the first and the second fluorescent radiation.

18 Claims, 2 Drawing Sheets

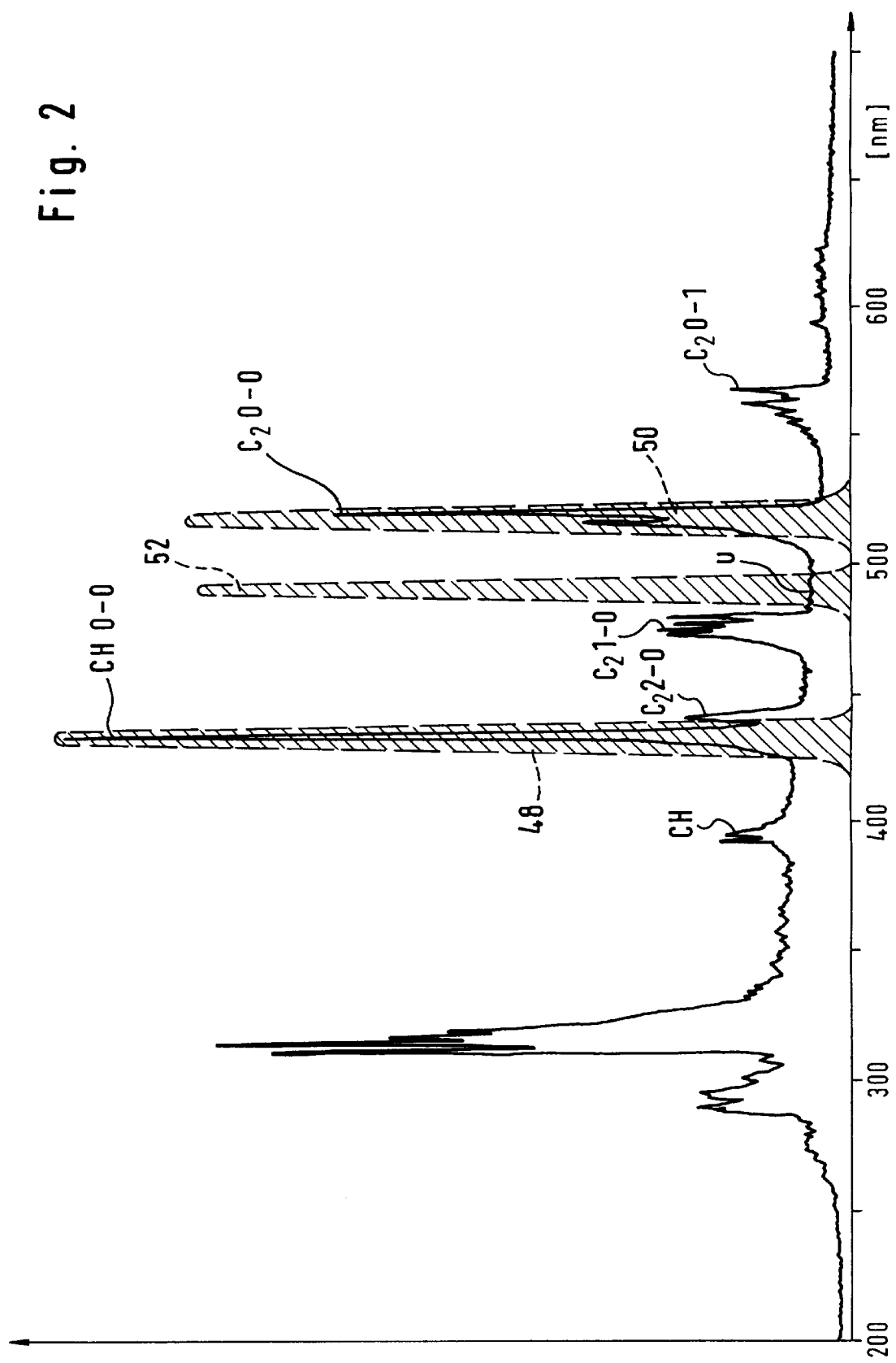

STOICHIOMETRIC RATIO MEASURING DEVICE

This application is a continuation of PCT/EP97/04244 filed Aug. 5, 1997.

The invention relates to a measuring device for determining stoichiometric ratios when burning hydrocarbons.

BACKGROUND OF THE INVENTION

All known measuring devices for determining stoichiometric ratios when burning hydrocarbons operate more or less satisfactorily, as no method which enables reliable information on the stoichiometric ratios to be obtained has yet been found.

SUMMARY OF THE INVENTION

The object of the invention is therefore to provide a measuring device by means of which stoichiometric ratios can be determined easily and reliably when burning hydrocarbons.

This object is achieved according to the invention with a measuring device of the type initially described in that a sensor is provided to detect an intensity of a first fluorescent radiation from C—H molecular fragments arising during the burning and a sensor is provided to detect an intensity of a second fluorescent radiation from molecular fragments arising during the burning and comprising only C atoms, that the sensors generate an intensity-dependent first and second sensor signal, respectively, on the basis of the first and the second fluorescent radiation, and that an evaluation circuit is provided which generates an output signal corresponding to a stoichiometric ratio from a ratio between the intensities of the first and the second fluorescent radiation.

The advantage of the solution according to the invention lies in the fact that this represents a very simple and reliable method for determining the stoichiometric ratio, as the intensity of the molecular fragments comprising only C atoms related to the intensity of the fluorescence of the C—H molecular fragments represents an accurate measure of the stoichiometric ratios, in particular the stoichiometric coefficient.

Where the molecular fragments comprising only C atoms are concerned, the fluorescence of the $C_2$ molecular fragments, i.e. the carbon dimers, is preferably detected at normal pressures, while the fluorescence of $C_3$ molecular fragments, i.e. carbon trimers, can be detected as an alternative to the fluorescence of $C_2$ molecular fragments when burning hydrocarbons at higher pressures, i.e. above 3 bar.

However in both cases the molecular fragments comprising only C atoms represent a sensitive measure of the stoichiometric ratios.

Since it is not just the fluorescence of the molecular fragments which is detected when burning hydrocarbon, but also the so-called background radiation resulting, for example, through thermal radiation, background radiation is present at a high level of intensity. It is for this reason that a particularly advantageous embodiment of the solution according to the invention provides a sensor to detect an intensity of background radiation arising during the burning and, furthermore, that the sensor generates an intensity-dependent third sensor signal and, before the ratio of the intensities measured at the wavelengths of the first and the second fluorescent radiation of the molecular fragments is formed, the evaluation circuit corrects these with respect to the intensity of the background radiation.

The determination according to the invention of the stoichiometric ratio is thus improved still further, as there is no distortion of the measured intensities at the wavelength of the fluorescence of the molecular fragments due to background radiation.

The sensors which detect the first and the second fluorescent radiation and the background radiation may be different sensors by means of which the intensity can be measured simultaneously. It is, however, also possible to use one sensor and for this to be acted upon in succession by the first and the second fluorescent radiation and the background radiation to measure the respective intensities.

The intensities may be corrected in any desired complex manner. However it is particularly advantageous if the evaluation circuit subtracts the third sensor signal from the first and the second sensor signal and thus eliminates the influence of the background radiation in a first approximation.

The intensity of the background radiation can be determined in a wide variety of ways. For example, it would be possible to determine the background radiation directly next to the fluorescence band measured at the time.

According to a particularly simple solution, however, the third sensor detects the intensity of the background radiation at a wavelength between that of the fluorescent radiation of the C—H molecular fragments and that of the molecular fragments comprising only C atoms. This measurement represents a good determination by approximation of the respective background radiation.

As regards the detection of the fluorescence by the sensors, no further details were provided in connection with the above illustration of the individual embodiments. It would, for example, be possible to dispose the sensors such that they directly detect the fluorescence when the hydrocarbons are burned.

However it is particularly expedient to deliver the fluorescence arising during the burning to the sensors via a light guide, as this offers the possibility of disposing the sensors at a distance from the burning and thus in an area which is more favourable in thermal terms.

In order also to protect the light guide from the high temperatures during burning, a protective window is preferably disposed before a front end of the light guide which faces the burning, a protective window of this kind also enabling the light guide to be protected against excessively high temperatures.

According to a particularly favourable solution, the fluorescence is detected by a single light guide and divided by means of a branch point into a branch for the detection of the first fluorescence, a branch for the detection of the second fluorescence and a branch for the detection of the background. This solution has in the first place the great advantage that the fluorescence detected at the time is detected by means of the sole light guide from the same solid angle and local differences in burning do not therefore affect the intensity of the first and the second fluorescence or of the background and, on the other hand, the advantage that the optical access which is required to detect the fluorescence from the burning, for example in a combustion chamber, is extremely limited in spatial terms.

No further details have yet been provided with regard to the determination of the fluorescence to be detected by the respective sensor. According to an advantageous solution, a wavelength-selective element is provided to determine the radiation intended for the respective sensor, so that only the selected radiation strikes the sensor and the remainder is blanked out.

The wavelength-selective element can basically be formed in any desired manner. A prism or a diffraction grating, for example, may be provided as the wavelength-selective element. As the device according to the invention should be of the simplest possible design, it is particularly advantageous for the wavelength-selective element to be an optical band-pass filter.

In order to achieve the best possible filter characteristic and suppress the unwanted radiation as effectively as possible, the optical band-pass filter is preferably an interference filter.

However the solution according to the invention does not just relate to a measuring device, the object according to the invention also being solved according to the invention with a regulating device for regulating the burning of hydrocarbons with an oxidizing agent in stoichiometric ratios, comprising a regulating circuit and at least one control valve, which can be activated by this circuit, for controlling a delivery of hydrocarbons or of oxidizing agent to the burning process in that the regulating circuit receives as input signal an output signal from a measuring device described above for determining stoichiometric ratios.

The object according to the invention is additionally solved by a measuring method for determining stoichiometric ratios when burning hydrocarbons in which an intensity of the fluorescent radiation from C—H molecular fragments arising during the burning and an intensity of the fluorescent radiation from molecular fragments arising during the burning and comprising only C atoms are measured according to the invention and the stoichiometric ratio when burning the hydrocarbons is determined from the ratio of the intensities of the fluorescent radiation.

The measuring method according to the invention has the same advantages as were illustrated in connection with the measuring device according to the invention.

In this case too it is particularly expedient for the intensities measured at the wavelength of the fluorescent radiation of the molecular fragments to be corrected with respect to the intensity of the background radiation arising during the burning, so that the distortion, due to this background radiation, of the intensities actually measured does not affect the accuracy of the measurement result.

The intensity of the background radiation can be determined in a wide variety of ways. The most precise procedure possible would be to determine the background radiation in each case directly next to the wavelength of the measured fluorescent radiation. However, according to a simplified solution, the intensity of the background radiation is measured between the wavelengths of the detected fluorescent radiations of the molecular fragments.

In order to obtain the largest possible signal, which is determined by the fluorescent radiation, the integral intensity of the fluorescence of a vibrational band of a molecular vibration of the respective molecular fragment is preferably measured, as this additionally improves the ratio of the measured intensity relative to the background radiation and the error still existing due to background radiation upon correcting the latter has minimal effects.

There are several possibilities regarding the intensity of the molecular fragments comprising only C atoms. For example, according to an advantageous solution, the intensity of the fluorescence of $C_2$ molecular fragments is measured, this preferably taking place when burning at normal low pressures. Alternatively, the intensity of the fluorescence of $C_3$ molecular fragments is measured—particularly when burning hydrocarbons at high pressures.

The following description and the representation in the drawings of an embodiment reveal further features and advantages of the invention.

BRIEF DESCRIPTION OF THE DRAWINGS

FIG. 1 is a diagrammatic representation of a measuring device according to the invention with a regulating device according to the invention for regulating the burning of hydrocarbons in stoichiometric ratios and FIG. 2 is a diagrammatic representation of the spectrum of the fluorescence of molecular fragments when burning hydrocarbons.

DETAILED DESCRIPTION OF THE INVENTION

Figure 1:
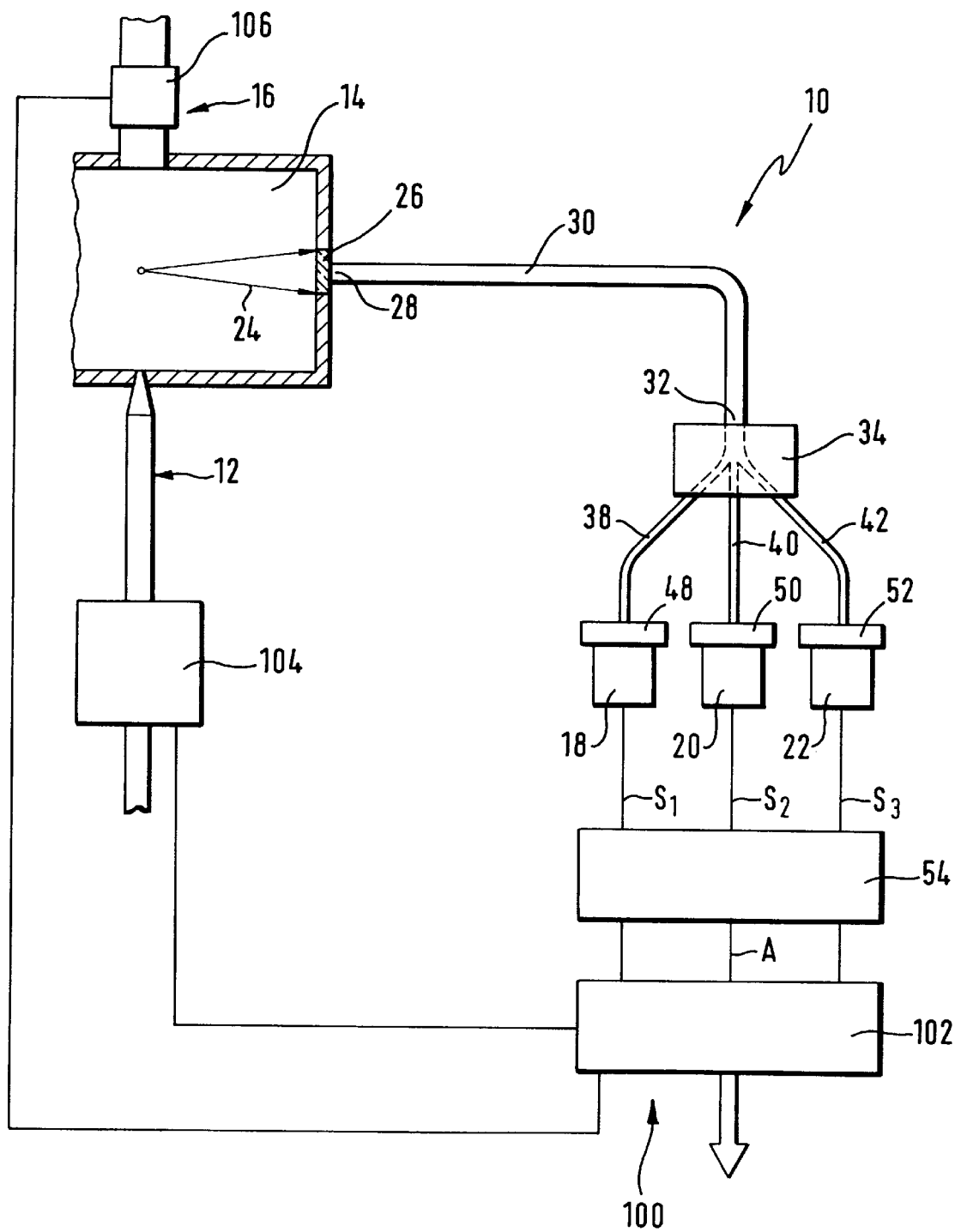

An embodiment represented in FIG. 1 of a measuring device, which is designated as a whole by 10, for determining stoichiometric ratios when burning hydrocarbons, which are delivered via a delivery device 12 to a combustion chamber 14, with an oxidizing agent, which is delivered via a delivery device 16, comprises a total of three photodetectors 18, 20 and 22 for detecting different fluorescence bands of the fluorescent radiation 24 resulting when burning the hydrocarbons in the combustion chamber 14. The fluorescent radiation 24 passes via a protective window 26 consisting, for example, of translucent $Al_2O_3$ or $Al_2O_3$ in the form of ruby into a first end 28 of a light guide which is designated as a whole by 30 and the second end 32 of which is connected to a beam splitter 34, which divides the fluorescence in equal parts, i.e. in the ratios 1/3 1/3 1/3, among three light guides 38, 40, 42, which then guide the fluorescence to the photodetectors 18, 20 and 22, with an interference filter 48, 50, 52 being connected upstream of each of the photodetectors 18, 20 and 22, which filter lets pass a certain wavelength range of the fluorescence for detection by the respective photodetector 18, 20, 22.

The fluorescence spectrum of the molecular fragments arising when burning hydrocarbon which are detected by the measuring device according to the invention exhibits a high number of spectral lines, with fluorescence bands of the carbon dimer molecule $C_2$ corresponding to the respective molecular vibration bands occurring in the visible range represented in FIG. 2. These are the fluorescence bands $C_2,0\text{-}1$, $C_2,0\text{-}0$, $C_2,1\text{-}0$ and $C_2,2\text{-}0$.

Fluorescence bands of CH molecular fragments also occur.

In the solution according to the invention the first sensor 18 detects the intensity of the fluorescent radiation of the CH,0-0 band of CH molecular fragments arising during the burning, for example at 431.5 nm. For this purpose the interference filter 48 is selected such that it essentially transmits the entire CH fluorescence band at 431.5 nm, although it rejects the adjacent $C_2,2\text{-}0$ band.

The second photodetector 20 detects the intensity of the fluorescent radiation of the $C_2,0\text{-}0$ band at 516.5 nm, and the interference filter 50 is accurately installed such that it essentially transmits the entire band.

The third photodetector 22 serves to detect the thermal radiation forming a background u. The interference filter 52 lies at a wavelength of 495 nm, for example, and therefore measures the background next to the $C_2,0\text{-}0$ fluorescence band, which can essentially be equated with the background u of the CH band.

Each of the photodetectors 18, 20 and 22 generates an output signal S1, S2, S3 which is proportional to the intensity of the respective fluorescence and delivers this to an evaluation circuit 54, which corrects the intensity measured by the first sensor 18 and the second sensor 20 in the $C_2$,0-0 band and the CH,0-0 band with respect to the background, with the intensity of the background u being subtracted from the intensity measured by the first photodetector 18 and the second photodetector 20 in the simplest case.

The evaluation circuit 54 then forms a ratio of the corrected intensities of the fluorescence of the $C_2$,0-0 fluorescence band and the CH,0-0 fluorescence band.

This is preferably effected in the evaluation circuit 54 by digital means, i.e. the output signals S1, S2, S3 of the photodetectors 18, 20, 22 are digitized and then further processed by a microcomputer provided in the evaluation circuit 54.

The ratio of the intensity of the $C_2$,0-0 band to the intensity of the CH,0-0 band at 431.5 nm provides a measure of the stoichiometric ratio when burning hydrocarbons in the combustion chamber, as a $C_2$,0-0 band which is intense relative to the CH,0-0 band represents an indication of an excessively rich mixture, which means the burning of hydrocarbon in excess.

A measuring device 10 of this kind according to the invention can preferably also be used in conjunction with a regulating device 100 comprising a regulating circuit 102 which in turn controls a supply valve 104 of the delivery device 12 for the hydrocarbon and a valve 106 of the delivery device for the oxidizing agent 16. This regulating circuit 102 is preferably supplied with the output signal A of the evaluation circuit 54, which output signal represents a measure of the stoichiometric ratio when burning the hydrocarbons in the combustion chamber 14. Depending on the range in which the stoichiometric ratio lies, it is possible to regulate the delivery of the hydrocarbon via the delivery valve 104 or of the oxidizing agent via the delivery valve 106 or both so as to achieve, as far as possible, an ideal stoichiometric ratio when burning hydrocarbons in the combustion chamber 14.

What is claimed is:

1. A measuring device for determining stoichiometric ratios when burning hydrocarbons, comprising:
    a first sensor to detect an intensity of a first fluorescent radiation connected to molecular vibration bands of C—H molecular fragments arising during the burning,
    a second sensor to detect an intensity of a second fluorescent radiation connected to molecular vibration bands of molecular fragments arising during the burning and comprising only C atoms,
    wherein the first and second sensors generate intensity-dependent first and second sensor signals, respectively, on the basis of the first and the second fluorescent radiation,
    an evaluation circuit which generates an output signal corresponding to a stoichiometric ratio from a ratio between the intensities of the first and the second fluorescent radiation, and
    a third sensor to detect an intensity of background radiation arising during the burning, wherein:
        the third sensor generates an intensity-dependent third sensor signal, and
        before the ratio of the intensities measured at the wavelengths of the first and the second fluorescent radiation of the molecular fragments is formed, the evaluation circuit corrects these intensities with respect to the intensity of the background radiation.

2. A measuring device according to claim 1, wherein:
    the evaluation circuit subtracts the third sensor signal from the first and the second sensor signal.

3. A measuring device according to claim 1, wherein:
    the third sensor detects the intensity of the background radiation at a wavelength between that of the first fluorescent radiation of the C—H molecular fragments and that of the second molecular fragments comprising only C atoms.

4. A measuring device according to claim 1, further comprising:
    a light guide for supplying the fluorescence arising during the burning to the sensors.

5. A measuring device according to claim 4, further comprising:
    a protective window disposed before a front end of the light guide which faces the burning.

6. A measuring device according to claim 4, wherein:
    the fluorescence can be intercepted by a single light guide and divided by means of a branch point into a branch for the detection of the first fluorescence, a branch for the detection of the second fluorescence and a branch for the detection of the background radiation.

7. A measuring device according to claim 1, further comprising:
    a wavelength-selective element to determine the radiation intended for the respective sensor.

8. A measuring device according to claim 7, wherein:
    the wavelength-selective element is an optical bandpass filter.

9. A measuring device according to claim 8, wherein:
    the optical band-pass filter is an interference filter.

10. A regulating device responsive to said output signal from the measuring device of claim 1 for regulating the burning of hydrocarbons with an oxidizing agent in stoichiometric ratios, comprising:
    a regulating circuit for receiving said output signal and at least one control valve controlled thereby for controlling a supply of hydrocarbons or oxidizing agent to the burning process.

11. A measuring method for determining stoichiometric ratios when burning hydrocarbons, comprising the steps of:
    measuring an intensity of a first fluorescent radiation connected to molecular vibration bands of C—H molecular fragments arising during the burning, and an intensity of a second fluorescent radiation connected to molecular vibration bands of molecular fragments arising during the burning and comprising only C atoms,
    determining the stoichiometric ratio when burning the hydrocarbons from the ratio of the intensities of the first and the second fluorescent radiation,
    measuring an intensity of background radiation arising during the burning, and
    correcting the intensities measured at the wavelength of the fluorescent radiation of the molecular fragments with respect to the intensity of the background radiation arising during the burning.

12. A measuring method according to claim 11, wherein:
    the intensity of the background radiation is measured between the wavelengths of the detected fluorescent radiation of the molecular fragments.

13. A measuring method according to claim 11, wherein:

the integral intensity of the fluorescence the vibrational band of a molecular vibration of the respective molecular fragment is measured.

14. A measuring method according to claim 11, wherein:

the intensity of the fluorescence of $C_2$ molecular fragments is measured.

15. A measuring method according to claim 11, wherein:

the intensity of the fluorescence of $C_3$ molecular fragments is measured.

16. A measuring method according to claim 11, wherein:

the integral intensity of the fluorescence of the vibrational band of a molecular vibration of the respective molecular fragment is measured.

17. A measuring method according to claim 11, wherein:

the intensity of the fluorescence of $C_2$ molecular fragments is measured.

18. A measuring method according to claim 11, wherein:

the intensity of the fluorescence of $C_3$ molecular fragments is measured.

* * * * *